United States Patent [19]
Oude Alink

[11] Patent Number: 5,840,942
[45] Date of Patent: Nov. 24, 1998

[54] CATALYZED SYNTHESIS OF ARYL-SUBSTITUTED FATTY ACIDS AND FATTY ESTERS AND COMPOSITIONS RELATED THERETO

[75] Inventor: Bernardus A. Oude Alink, St. Louis, Mo.

[73] Assignee: Baker Hughes Incorporated, Houston, Tex.

[21] Appl. No.: 375,217

[22] Filed: Jan. 19, 1995

Related U.S. Application Data

[63] Continuation-in-part of Ser. No. 161,826, Dec. 2, 1993, Pat. No. 5,440,059.

[51] Int. Cl.$^6$ ...................................................... C11C 3/00
[52] U.S. Cl. ........................... 554/162; 554/161; 554/163
[58] Field of Search ................................... 554/161, 163, 554/220

[56] References Cited

U.S. PATENT DOCUMENTS 5,034,161  7/1991  Alink ...................................... 260/413

FOREIGN PATENT DOCUMENTS 62-10040  1/1987  Japan .............................. C07C 57/30

OTHER PUBLICATIONS

English Translation of JP–62–10040, Jan. 19, 1987.
Chemical Abstracts, vol. 107, 1986, 96439.

*Primary Examiner*—Gary Geist
*Assistant Examiner*—Deborah D. Carr
*Attorney, Agent, or Firm*—Howell & Haferkamp, L.C.

[57] ABSTRACT

A novel method for preparing an aryl-substituted fatty acid or fatty ester is disclosed. According to the method, an olefinic composition selected from among mono-unsaturated fatty acids, mono-unsaturated fatty esters and mixtures thereof is introduced to a reaction zone comprising a liquid aromatic hydrocarbon and a catalytic amount of a clay catalyst to produce a reaction that is allowed to proceed for a time and at a temperature sufficient to produce a reaction product comprising a desired yield of aryl-substituted fatty acid or fatty ester. Preferably, the introduction of the olefinic composition is conducted slowly, such as over a period of one to four, more preferably, two to four, hours. Related methods and compositions, including xylyl-stearic acid, are also disclosed.

33 Claims, No Drawings

CATALYZED SYNTHESIS OF ARYL-SUBSTITUTED FATTY ACIDS AND FATTY ESTERS AND COMPOSITIONS RELATED THERETO

This is a continuation-in-part application of application U.S. Ser. No. 08/161,826, filed Dec. 2, 1993, now U.S. Pat. No. 5,440,059.

BACKGROUND OF THE INVENTION

1. Field of the Invention

The present invention relates to aryl-substituted fatty acids and fatty esters, and more particularly to the clay- or zeolite-catalyzed synthesis of such compositions wherein the aryl group is an aromatic hydrocarbon and to compositions prepared by means of such synthesis.

2. Description of the Prior Art

Aryl-substituted fatty acids and fatty esters are useful in a number of applications. Branched saturated acids are recognized as lubricants for many applications and are employed in paint formulations (such as automobile paint), soaps and metal salts and also have been found to be useful as corrosion inhibitors or as substrates for corrosion inhibitors. Saturated fatty acids have been considered for such uses; but they are ordinarily solids which are insoluble in the oil products, such as motor oil, for which the inhibitors are desired. Thus, branched acids, such as iso-stearic acid, sometimes have been used. Aryl-substituted saturated fatty acids and fatty esters are especially desirable because they are liquids that have superior oil solubility. It is desirable to modify soybean or other naturally occurring oils with such aryl-substitution to make them better diesel fuels.

However, conventional methods for preparation of aryl-substituted fatty acids and fatty esters suffer from several drawbacks. For example, standard methods not only have involved production of complex reaction mixtures and required expensive and cumbersome separation techniques, but also result in low yields. As a result, such substituted acids and esters are expensive to produce. And preparation of such substituted acids and esters is particularly problematic where the aryl substituent is an aromatic hydrocarbon such as xylene, cumene, toluene or benzene. This is because such hydrocarbons are significantly less reactive than other aryl groups such as phenol, leading to significantly lower yields.

Typically, a Friedel-Crafts reaction has been the vehicle for preparation of aryl-substituted saturated acids in which the aryl substituent is an aromatic hydrocarbon. According to this reaction, an aromatic hydrocarbon, such as benzene, xylene, cumene or toluene, is reacted in the presence of an acidic reagent with an unsaturated aliphatic acid, for example, oleic acid. The acidic reagent employed in this process is a strong Lewis acid, commonly aluminum chloride, boron trifluoride or hydrofluoric acid. For example, in Nakano, Y. and Foglia, T. A., "Methanesulfonic Acid Catalyzed Addition of Aromatic Compounds to Oleic Acid," JAOCS, Vol. 61, No. 3 (March 1984), the use of aluminum chloride to catalyze a reaction between benzene and oleic acid is noted.

Such methods involve several disadvantages. For example, since the Lewis acids employed in the Friedel-Crafts reaction are extremely strong acids and are extremely reactive, and because hydrogen halide gas is generated, special handling and extra safety precautions are required. In addition, the reaction is exothermic and must be moderated by cooling. Further, the Lewis acid is consumed in the reaction, making recycling of the acid impossible and adding significantly to the cost of the reaction. Moreover, such methods produce inferior yields when the aliphatic acid is internally unsaturated.

In addition, the reaction also is associated with several undesirable side reactions, resulting in limited yields and separation problems. Moreover, for example, since one such side reaction is polyalkylation, a substantial excess of the aromatic hydrocarbon is commonly employed in an effort to limit polyalkylation of the aromatic ring. However, such efforts to limit polyalkylation have proven unsatisfactory since use of a substantial excess of the aromatic hydrocarbon tends to increase costs of the process and, in any event, polyalkylation is not entirely eliminated by such measures.

According to other side reactions, where an acid such as oleic acid is employed as an aliphatic hydrocarbon substrate in the reaction, the intermediate carbonium ion reacts with the carboxyl group of the acid to form lactones. If an unsaturated acid is employed as the aliphatic hydrocarbon substrate, the intermediate carbonium ion may also react with two acid molecules to yield an ester of the acid. As a result of the involvement of such side reactions, the yield of the desired product is diminished and the reaction product comprises a mixture of compounds, requiring extensive purification techniques to isolate the desired mono-substituted alkyl aromatic.

Moreover, many procedures required by the conventional reaction prove very troublesome in practice. The reaction products are darkly colored, making separation and isolation difficult; and steam distillation is often necessary to isolate the desired products. In addition, the products obtained are complex mixtures; and their complex structure adds to the difficulty in purification. Not only that, but also the excess highly reactive Lewis acid which is employed in the reaction as a catalyst must be carefully quenched.

Further, the physical properties of the reaction product are often not suitable for the desired applications. For example, the typical reaction yields a high melting solid, when commercial application, for example, as a corrosion inhibitor or substrate therefor, requires a low melting solid or a liquid. Thus, an improved method for preparation of suitable branched fatty acids is needed.

The Nakano and Foglia article noted above describes a method for adding aromatic compounds to the double bond oleic acid by a methanesulfonic acid catalyzed reaction. However, the reaction described therein requires copious amounts of methanesulfonic acid (6:1 molar ratio based on oleic acid content) and produces yields significantly under 80%, resulting in a difficult separation process involving a two-step extraction/water washing technique and a relatively expensive process. Moreover, the significant interplay of undesirable side reactions in the Nakano and Foglia method results in a product containing large amounts of impurities, especially lactones and esters of oleic acid.

Kohashi and Foglia have disclosed a method utilizing bentonite clay to catalyze a reaction between phenol and oleic acid, resulting in a 96% yield of an alkylphenol addition product. See Kohashi and Foglia, T. A., "Addition of Aromatic Compounds to Oleic Acid Catalyzed by Heterogeneous Acid Catalysts," JAOCS, Vol. 61, No. 6 (June 1984). However, as noted above, aromatic hydrocarbons are extremely unreactive compared to phenol. In fact, aromatic hydrocarbons such as benzene, toluene, xylene, cumene and so forth are so unreactive that they are among the most commonly used organic solvents. Thus, Kohashi and Foglia report that the use of toluene as the aromatic produces less than a 2% yield of alkylbenzene addition product. Accordingly, the method of Kohashi and Foglia does not appear to be a practical alternative for synthesis from aromatic hydrocarbons.

Japanese Patent Publication No. Tokkai Sho62-10040 discloses another method for preparation of aryl fatty. In that method, an activated clay catalyst is used in combination with a phosphorus oxyacid. Experimental results reported in the publication show an increase in yield when the phosphorus oxyacid is used. With phenol as the aryl compound, yields of less than 80% are reported in the absence of the phosphorus oxyacid, although a high yield appears to be reported in one trial in which the phosphorus oxyacid is replaced with a straight-chain $C_{12}$ alkyl benzenesulfonic acid. With anisole as the aryl compound, the presence of the phosphorus oxyacid was reported to have increased yield from about 26.9% to about 72.6%. On the other hand, when an aromatic hydrocarbon, toluene, was used, the reported yield even for the reaction carried out in the presence of a phosphorus oxyacid was still significantly less than 70% (actually, 61.7%); but even that represented an increase from the 31.2% yield reported for the reaction carried out in the absence of a phosphorus oxyacid.

Accordingly, the industry is still searching for satisfactory high yield, low cost methods for preparation of aryl-substituted fatty acids and fatty esters derived from aromatic hydrocarbons and fatty acids and fatty esters. Moreover, the low reactivity of aromatic hydrocarbons and the resulting difficulties in synthesizing aryl-substituted fatty acids and fatty esters from such hydrocarbons has limited the variety of aryl-substituted fatty acids and fatty esters available for use, and some, such as xylylstearic acid, are believed to have not even been synthesized.

SUMMARY OF THE INVENTION

The present invention, therefore, is directed to a novel method for preparing an aryl-substituted fatty acid or fatty ester. According to the method, an olefinic composition selected from among mono-unsaturated fatty acids, mono-unsaturated fatty esters and mixtures thereof is introduced to a reaction zone comprising a liquid aromatic hydrocarbon and a catalytic amount of a clay or zeolite catalyst to produce a reaction that is allowed to proceed for a time and at a temperature sufficient to produce a reaction product comprising at least a 70% yield of aryl-substituted fatty acid or fatty ester. The present invention is also directed to similar methods carried out without phosphorus oxyacids or in which the catalyst consists essentially of a zeolite or clay catalyst and the yield is at least 50%. Preferably, the introduction of the olefinic composition is conducted slowly, such as over a period of one to four, more preferably, two to four, hours. The introduction may be conducted, for example, at a generally constant flow rate over that period or in small, discrete doses.

The present invention is also directed to a novel method for preparing an aryl-substituted fatty acid or fatty ester, comprising a first and a second step. In the first step, a liquid aromatic hydrocarbon is brought into contact with a catalytic amount of zeolite or a clay selected from among Montmorillonite K10, Clarion 470 and Clarion 550 to form a catalyzed aromatic composition comprising clay and aromatic liquid hydrocarbon. In the second step, an olefinic composition selected from among mono-unsaturated fatty acids, mono-unsaturated fatty esters and mixtures thereof is added, over a period of at least about an hour, to the catalyzed aromatic composition, while the catalyzed aromatic composition is maintained at a temperature sufficient to produce a reaction product comprising a 70% yield of aryl-substituted fatty acid or fatty ester.

The present invention is further directed to a novel composition of matter comprising xylylstearic acid and to xylylstearic acid itself.

Among the several advantages of this invention, may be noted the provision of a method for preparing aryl-substituted fatty acids or esters more economically than is accomplished with conventional processes; the provision of such method that employs low-cost catalysts; the provision of such methods that results in high yields of aryl-substituted fatty acids and fatty esters; the provision of such method that permits high yield production of such aryl-substituted compositions from relatively unreactive aromatic hydrocarbons; and the provision of new compositions, the production of which is enabled by such method.

DETAILED DESCRIPTION OF THE PREFERRED EMBODIMENTS

In accordance with the present invention, it has been discovered that by the use of certain very inexpensive zeolite or clay catalysts, mono-unsaturated fatty acids and fatty esters can be reacted with aromatic hydrocarbons—even aromatic solvents generally considered to be extremely unreactive—to produce surprisingly high yields of aryl-substituted fatty acids and fatty esters, particularly if the aromatic hydrocarbon is added to the clay catalyst before addition of the fatty acid or ester and especially if the fatty acid or ester is then added slowly to the aromatic hydrocarbon and catalyst. Moreover, after the reaction has been completed, the catalyst may be separated out by simple filtration and, because the catalyst is so inexpensive, salvage for reuse need not even be of concern. Thus, a technique has been discovered that not only produces high yields of aryl-substituted fatty acids and fatty esters, but does so far more economically, without the need for phosphorus oxyacids, and with a wider variety of cyclic compositions than do conventional processes, and without the variety of drawbacks of such processes. As a result, certain compositions, such as xylylstearic acid, that are believed to have been previously unavailable now can be produced at low cost.

Thus, whereas Kohashi and Foglia reported an aryl-substituted fatty acid yield of less than 2% associated with the aromatic hydrocarbon toluene and a bentonite clay catalyst, the methods of the present invention can use catalysts, even clay catalysts, to produce aryl-substituted fatty acid and fatty ester yields of over 50%, and even near 100%, with aromatic hydrocarbons. In the method of Kohashi and Foglia, oleic acid and toluene (or phenol) are mixed together and bentonite clay is added to the mixture. The present inventor has now discovered that far superior yields may be obtained simply by first mixing the clay catalyst with the aromatic hydrocarbon and thereafter introducing the fatty acid or fatty ester to the aromatic hydrocarbon and clay catalyst mixture, and that even higher yields may be obtained by introducing the fatty acid or fatty ester slowly, such as over a period of over an hour or two. Moreover, it has now been found that other types of clay catalysts produce surprisingly higher yields than does bentonite clay.

While the present inventor does not wish to be bound to any particular theory of operation, it is believed that if the fatty acid (or ester) contacts the clay catalyst first or simultaneously with the aromatic hydrocarbon, the acid (or ester)

bonds to the catalyst surface and close proximity of fatty acid (or ester) molecules thus bonded results in interreaction between the molecules, thus forming undesirable side products instead of the desired aryl-substituted product. Thus, contacting the clay first with the aromatic results in bonding of the aromatic hydrocarbon to the clay surface. An excess of aromatic hydrocarbon is preferred to ensure monopolization of the surface by the aromatic hydrocarbon, thereby reducing or eliminating the availability of sites on the clay surface to which the fatty acid (or ester) may bond. Monopolization of the surface by the aromatic hydrocarbon is further ensured by adding the fatty acid (or ester) slowly.

As noted, the new process also involves the use of zeolite or certain clay catalysts. The clay catalysts are acid clay catalysts of the type known for their usefulness in dimer acid synthesis. Such clay catalysts are solids, typically in the form of powder.

Surprisingly, it has been found that the efficiency of the reaction differs substantially depending on the particular clay catalyst employed. For example, while some clay catalysts, such as Montmorillonite KSF, bentonite (as employed by Kohashi and Foglia), Kaolin, Panther Creek clay and talc, have not been found to be very active and tend to favor formation of dimer acids, highly efficient reactions resulting in nearly quantitative yields are associated with clays identified by the trade designations Clarion 470 and Clarion 550 clays (sold by American Colloid Company) and Montmorillonite K10 clay. This high activity of Montmorillonite K10 clay is especially surprising in view of the relative low activity of Montmorillonite KSF clay, which is believed to differ from Montmorillonite K10 clay only in the greater surface area of the K10 variety. The surface area of the K10 type is reported to be about 220 to about 270 $m^2/gm$, while the surface area of the KSF type is reported to be about 20 to about 40 $m^2/gm$. Thus, surface area seems to play a role and a surface area of greater than 40 $m^2/gm$, preferably greater than about 100 $m^2/gm$, especially more than about 200 $m^2/gm$, such as about 200 to about 300 $m^2/gm$ is preferred. Although a satisfactory theory explaining the differences in activity among the types of clay catalysts has not been developed, it is suspected that higher activity may lie in the higher acidity and better absortivity of some clays as well as in greater surface area.

Aromatic hydrocarbons have been found to be extremely unreactive. While prior art methods have been successful to some degree in effecting reactions with the far more reactive compositions such as phenol, they have been quite unsatisfactory in obtaining acceptable or even any yields of aryl-substituted fatty acids and fatty esters from aromatic hydrocarbons such as the solvents toluene, xylene, benzene, cumene and the like, especially at low cost. Thus, it is believed that reaction of xylene with oleic acid to form xylylstearic acid has never before been carried out. The method of this invention permits low cost high yield from such relatively unreactive aromatics. In fact, it has been found that aromatics that contain hetero atoms are deleterious to the clay catalyst and so aromatic hydrocarbons are preferred for this method. Such hydrocarbons are liquids and include not only the preferred benzene-based aromatics as noted above, but other benzene-based hydrocarbons and polyaromatics such as naphthalenes and even anthracenes as well.

With respect to xylene, it has been found that the reaction rates and yields for the various isomers do not follow the expected electronic or steric rules. Instead, the rates and yields have been found to relate to the specific absorption of the aromatic and fatty acid (fatty ester) moieties on the clay. As a result, a higher rate of reaction has been noted with respect to ortho-xylene than with respect to meta-xylene, which in turn has been associated with a higher rate than has para-xylene.

The following discussion will refer to fatty acids, but may be applied to the esters thereof as well. The esters are generally liquid glycerides or liquid alkyl esters of the fatty acids which contain an alcohol-derived alkyl group of up to about ten carbon atoms, preferably up to about eight carbon atoms, such as methyl, butyl or ethylhexyl esters, as might be found in, for example, vegetable oils like soybean oil or corn oil.

The fatty acids employed in this reaction are mono-unsaturated liquids. They may be liquids by virtue of their natural state or as the result of melting a solid, dissolving a gas or solid in an organic solvent (which may be the same as the aromatic reactant), or compressing a gas. Preferably, the fatty acid is a liquid in its natural state.

The mono-unsaturated fatty acid (or the fatty acid derived moiety of a fatty ester) may be of any length of from four to about 22 carbon atoms, preferably about 14 to 22 carbon atoms, most preferably, about 18 carbon atoms. Thus, oleic acid is a particularly preferred species. Although the fatty acid is generally straight chained, it may contain a methyl branch or two as in iso-oleic acid. The fatty acid may be in a composition such as (especially in the case of fatty esters) a vegetable oil like corn oil or soy bean oil and so forth, but the presence of poly-unsaturated (i.e., two or more double bonds) fatty acids is undesirable as it may lead to the formation of by-products such as dimers. Thus, it is desired that poly-unsaturated fatty acids (such as linoleic acid) not be present at a level of more than about 10% by weight, preferably no more than about 5% by weight, more preferably no more than about 2% by weight of the mono-unsaturated acid(s). Optimally, the composition would be free of poly-unsaturated acids.

The reaction may be carried out as follows. As explained above, it has been found that mixing the aromatic hydrocarbon and fatty acid (or ester) together and then introducing the clay to the mixture, or exposing the clay to the fatty acid (or ester) before introduction of the aromatic hydrocarbon results in poor yield of the desired aryl-substituted compound. Exposing the clay to the aromatic hydrocarbon before introduction of the fatty acid (or ester) has been found to result in vastly improved yield. Thus, the clay catalyst first should be exposed to the aromatic hydrocarbon. Typically, the clay is in the form of a powder and exposure is accomplished simply by mixing the powder into the aromatic hydrocarbon. Clays have been found to differ dramatically in their activities and those having superior activities have been noted earlier in this specification.

An amount of aromatic hydrocarbon at least equimolar to the fatty acid (or ester) should be used and, preferably, an excess of aromatic hydrocarbon is employed. In other words, more than a mole (such as about five to about 100 moles, preferably about ten to about 75, more preferably about ten to about fifty, moles) of aromatic hydrocarbon is used per mole of fatty acid (or ester) that will be added. This aids in preventing the fatty acid (or ester) from contacting the clay. The clay catalyst is incorporated in an amount of from about 0.5 to about 4 parts by weight, preferably about 1 to about 2 parts by weight, per part by weight fatty acid (or ester) that will be added. It has been found that the higher the temperature the reaction is carried out, the less catalyst required.

Preferably, the mixture of aromatic and clay is refluxed for removal of water and then maintained at an elevated temperature of from about 130° C. to about 250° C., while the fatty acid (or ester) is added. It has been found that far higher yields, even up to quantitative, may be achieved by adding the fatty acid (or ester) slowly, such as over a period of more than about an hour, such as about one to about six, preferably about two to about four hours. The reaction mixture should be stirred continuously and the reaction carried out in a closed container, so that autogenous pressure reaches from about 50 to about 200 psig.

The reaction results in the elimination of the double bond in the mono-unsaturated fatty acid or ester. Therefore, the aryl-substituted fatty acid or fatty ester product is a liquid that is a saturated aliphatic terminating in a carboxyl group (a carboxylic acid) or its ester, with a hydrogen substituted with the aromatic group. Thus, for example, reaction with oleic acid yields an arylstearic acid. By-products may include other mono-unsaturated fatty acids, gamma lactone of stearic acid and dimer and higher acids. Dimerization and trimerization are the most undesirable side reactions.

The clay may be separated from resulting product by simple filtration and the excess aromatic hydrocarbon may be removed by evaporation. The clay may also be washed with organic solvent for further product recovery. The process of this invention has been found to be capable of extremely high yields, such as over 50%, typically over 60%, for example, at least 70%, especially over 80%, of the aryl-substituted product. In fact, by proper selection of the clay as noted above and slow addition of the fatty acid (or ester) to a clay and aromatic mixture, yields over 90%, generally over 95% and even near quantitative may be achieved. Because an excess of aromatics is used, yields described herein are based on moles of fatty acid or fatty ester employed, but generally correspond to the theoretical production of aryl-substituted fatty acid or ester if complete conversion were to take place.

Thus, such yields even of xylylstearic acid have been produced where the aromatic is xylene and the fatty acid is oleic despite the apparent inability of the industry to induce such reaction, at least on a practical scale, with an aromatic solvent such as xylene.

After filtering and evaporation, aryl-substituted fatty acid or fatty ester products of greater than 80% by weight, preferably greater than 90% by weight, and even greater than 95% by weight, purity are possible.

The aryl-substituted fatty acids and esters, especially xylylstearic acid, a useful for many applications. For example, xylylstearic acid may be used as a substituted for naphthenic acid as a corrosion inhibitor base or substrate, as an auto paint, soap or metal salt additive and as a lubricant in other formulations as well.

The following examples describe preferred embodiments of the invention. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples. In the examples, all percentages are given on a weight basis unless otherwise indicated.

EXAMPLE 1

Granular Montmorillonite K-10 clay (22 gm), Pamolyn-100 (a high grade—i.e., 91% pure—oleic acid from Hercules Corp.) (21.4 gm) and a mixture of xylenes (307.5 gm) were charged to an autoclave, stirred and heated for 70 hours at 450° F. (232° C.) and 130 to 140 psig autogenous pressure. After cooling to ambient temperature, the product was filtered and the catalyst washed with xylene. The washings were combined with the original product solution and evaporated under a vacuum. The yield, 26.9 grams, was analyzed by infrared, HNMR and CNMR spectroscopy. Analysis by GC showed xylylstearic acid as the main product (55%), with some unidentified acids lower than $C_{18}$ (40%) and very little dimer (less than 6%).

EXAMPLE 2

A mixture of Montmorillonite K10 (11.5 gm) clay in xylene (boiling point=142° C.) (104.7 gm) was refluxed under azeotropic conditions for a half hour. Pamolyn-100 (5.4 gm) was added and the resulting mixture refluxed and azeotropic condition continued for 22 hours. The mixture was then cooled to ambient temperature and filtered and evaporated under a vacuum to remove excess xylene. The resulting product (5.2 gm) was analyzed. Analysis by GC showed the product to comprise 80.2% xylylstearic acids, 11.8% $C_{18}$ acids, 4.1% dimer acid, 0.5% trimer acid and 2.9% unknown acid.

EXAMPLE 3

Five test runs were conducted in which Pamolyn-100 was refluxed in xylene with various clay catalysts. For each run, clay (100 gm) and xylene (250 gm) were placed in a 1-liter three-necked flask equipped with a mechanical stirrer, Dean Stark tube, reflux condenser and thermometer. The mixture was refluxed under azeotropic conditions until no more water was produced (0.5 to 1 hour). Then Pamolyn-100 (50 gm) was introduced all at once and the refluxing under azeotropic conditions was continued. At certain time intervals, samples were withdrawn for GC analysis. At the completion of the run, the reaction mixture was cooled to ambient temperature and filtered through Whatman No. 1 filter paper. The clay was washed with xylene and the xylene washings were combined with the filtered reaction mixture and evaporated under a vacuum to remove the excess xylene. The resulting products were then analyzed by standard techniques. The clay for each run was then washed with methanol and the methanol in the filtrate was evaporated under a vacuum to yield a product, referred to as the "methanol wash product", which was also analyzed by standard techniques. Finally, the clay for each run was dried in an oven at about 70° C. and the weight noted. The results were as follows, with "Time" representing the time in minutes following addition of the Pamolyn-100 and "% Xylylstearic Acid" being the percentage of the reaction product that was xylylstearic acid:

| | % Xylylstearic Acid for the Following Clays: | | | | |
|---|---|---|---|---|---|
| Time | Mont.* K10 | Mont.* KSF | Bentonite | Kaolin | Talc |
| 0 | 0 | 0 | 0 | 0 | 0 |
| 60 | 57 | 3 | 2 | 9 | 0 |
| 120 | 64 | 4 | 3 | 11 | 0 |
| 180 | 69 | 6 | 4 | 13 | 1 |
| 240 | 73 | 6 | 5 | 14 | 0 |
| 300 | 75 | 7 | 7 | 15 | 0 |
| 360 | 77 | 7 | 7 | 16 | 0 |
| 420 | 78 | 7 | 7 | 16 | 1 |
| 500 | 79 | 7 | 9 | 16 | 1 |
| 630 | 81 | 7 | 9 | 17 | 1 |

*Montmorillonite

EXAMPLE 4

Three test runs were conducted according to the procedure of Example 3, above, with Montmorillonite K10 as the clay. In one run, the xylene used was pure para-xylene, in another the xylene was pure meta-xylene, and in the third the xylene was pure ortho-xylene. The para-xylene reacted with the oleic acid to form, after conversion to the methyl esters for analytical purposes, 7.9% methyl ester of 17-xylylstearic acid, 2.8% methyl esters of 16-xylylstearic acid, 3.3% 15-xylylstearic acid, 4.3% 14-xylylstearic acid, 36.4% of a combination of 2- through 13-xylylstearic acid, 19.9% methyl esters of palmitic and stearic acids, 25.2% $C_{18}$ mono-unsaturated fatty acid and 1.9% gamma lactone of stearic acid. The meta-xylene reacted with the oleic acid to form 6.8%, 5.2%, 4.9% and 6.8% methyl esters of 17-, 16-, 15- and 14-xylylstearic acid, respectively, 5.4% xylylstearic acid in which the point of substitution could not be determined, 56.8% of a combination of 2- through 13-xylylstearic acid similar to that noted with the para-xylene, and 14.1% palmitic and stearic acids. The ortho-xylene reacted with the oleic acid to form 4.4%, 4%, 4.2% and 14.6% methyl esters of 17-, 16-, 15- and 14-xylylstearic acid, respectively, 64.8% of a combination of 2- through 13-xylylstearic acid similar to that noted with the para-xylene, and 8% methyl ester of stearic acid. It is believed that the methyl esters of palmitic and stearic acids in the products for each of the xylenes are present as a result of the presence of saturated acids in the Pamolyn-100. The specification for Pamolyn-100 allows up to 3% saturated fatty acid and 7% linoleic acid.

The following table indicates the rates of formation of xylylstearic acid ("X/S") and dimer or higher acids ("Dimer") for each of the xylenes in terms of the percentage each made up of the products formed at the noted number of hours after initiation of the reaction.

| Xylene | Product | 0 | 1.5 | 3 | 5 | 7 | 12.5 | 22 | 48 |
|---|---|---|---|---|---|---|---|---|---|
| Para- | X/S | 0 | 17 | 24 | 27 | 31 | 35 | 42 | 45 |
|  | Dimer | 0 | 8 | 12 | 12 | 10 | 15 | 10 | 12 |
| Meta- | X/S | 0 | 44 | 58 | 67 | 71 |  | 87 | 90 |
|  | Dimer | 0 | 9 | 10 | 10 | 10 |  | 10 | 10 |
| Ortho- | X/S | 0 | 75 | 86 | 90 |  |  | 90 |  |
|  | Dimer | 0 | 14 | 7 | 10 |  |  | 10 |  |

The tests conducted with the various xylenes, therefore, resulted in a xylylstearic acid distribution as follows, where the percentages represent the percentage the noted isomer (identified by the location of the substitution—that is, for example, %C-17 refers to the percentage of 17-xylylstearic acid) makes up of the total amount of xylylstearic acid:

| Xylene Used | %C-17 | %C-16 | %C-15 | %C-14 | %C-2 to C-13 |
|---|---|---|---|---|---|
| para-xylene | 14.4 | 5.1 | 6.0 | 7.9 | 66.7 |
| meta-xylene | 8.0 | 6.0 | 5.7 | 7.9 | 72.4 |
| ortho-xylene | 4.4 | 4.2 | 5.2 | 16.2 | 70.1 |

EXAMPLE 5

Montmorillonite K10 clay (20.1 gm), Pamolyn-100 (40.1 gm) and xylene (506.9 gm) were placed in a 1-liter "Chemco" reactor. The reactor was closed and the mixture was stirred and heated for 17 hours under autogenous pressure (41 psig max.) at 180 to 190° C. After allowing the mixture to cool to ambient temperature, the contents of the autoclave were filtered and the clay was washed with methanol. The methanol and xylene solutions were combined to yield a product that was found by HNMR to contain 94% xylylstearic acid and 6% diner acids. Thus, while a 2:1 weight ratio of clay to oleic acid was required when the reaction was conducted at 141°–145° C., a 1:2 weight ratio of clay to oleic acid was sufficient when the reaction was carried out at 180°–190° C. The reaction was repeated at 180°–190° C. with a clay to Pamolyn-100 weight ratio of 1:10. A sample withdrawn after 17 hours was analyzed by HNMR and found to contain 56% xylylstearic acid and 44% of a $C_{18}$ mono-unsaturated fatty acid. Continuing the reaction for 26 more hours did not increase the yield of xylylstearic acid.

Further increasing the reaction temperature to 232° C. allowed the reaction to proceed at a 1:10 clay to Pamolyn-100 ratio. At that temperature, in addition to the dimers, unidentified mono-acids with retention times similar to those of $C_{18}$ acids were observed by GC analysis. Montmorillonite K10 clay (8.5 gm), Pamolyn-100 (84.7 gm) and xylene (267.7 gm) were placed in a 450 ml stainless steel autoclave and heated with stirring for 19.5 hours at 232° C. The autogenous pressure reached a maximum of 110 psig during the reaction. After the mixture was allowed to cool to ambient temperature, the mixture was filtered. The clay was washed several times with xylene and the xylene solutions were combined and evaporated under a vacuum to yield 102.5 grams of product that was analyzed by HNMR, showing the presence of 61% xylylstearic acid. Analysis by GC indicated 60% xylylstearic acids, 14.4% dimer and higher acids and 25.3% mono-acids with a retention time indicative of about $C_{18}$ acids.

Further lowering the clay to Pamolyn-100 ratio to 1:79 and conducting the reaction at 232° C. for 19 hours produced a product containing only 6.3% xylylstearic acid according to GC analysis.

EXAMPLE 6

Clarion 550 clay (100 gm) and xylene (250 gm) were charged into a three-necked 1-liter round bottom flask equipped with a Dean Stark tube, reflux condenser and mechanical stirrer. The mixture was refluxed under azeotropic conditions at 142° C. until no more water was produced (1 hour). Pamolyn-100 (50 gm) was added all at once to the refluxing mixture and the reflux was continued for 48 hours, during which time samples were withdrawn periodically. The samples were analyzed by GC. At the end of the 48 hours, the mixture was cooled to ambient temperature and filtered and the clay was washed with xylene. The xylene washings were combined and evaporated under a vacuum to yield 41 grams of product. The clay then was washed with methanol and the methanol solution was evaporated in a vacuum to yield 10.4 grams of a second product. The clay was oven dried to yield 85.1 grams of material. Analysis of the first product by GC showed 4.7% palmitic and stearic acids, 92.4% xylylstearic acid, and 1.9% dimer and higher acids. Analysis of the second product by GC showed 20.3% $C_{18}$ acids, 6.4% gamma-lactone of stearic acid, 49% xylylstearic acid, and 24.4% diner and higher acids.

EXAMPLE 7

The procedure of Example 6, above, was repeated with Clarion 470 clay in place of the Clarion 550 clay, and again with Montmorillonite K10 clay as the catalyst. Products containing the following percentages of xylylstearic were obtained at the noted number of hours after addition of Pamolyn-100 for the noted clays:

|  | % Xylylstearic Acid | |
| --- | --- | --- |
| Hours | Clarion 470 | Mont.* K10 |
| 0 | 0 | 0 |
| 2 | 82 | 60 |
| 3 | 90 | 64 |
| 8 | 90 | 75 |
| 24 | 91 | 80 |

*Montmorillonite

The product contained about 5% dimer and higher acids and 5% palmitic and stearic acids at the end of the trial with Clarion 470 clay.

EXAMPLE 8

The procedure of Example 6, above, was carried out again for two trials, one with Clarion 470 clay and the other with Clarion 550 clay. The results were as follows, as shown in the form of the table in Example 7, above.

|  | % Xylylstearic Acid | |
| --- | --- | --- |
| Hours | Clarion 470 | Clarion 550 |
| 0 | 0 | 0 |
| 2 | 39 | 35 |
| 3 | 46 | 43 |
| 8 | 58 | 52 |
| 24 | 66 | 63 |

The percentage of dimer and higher acids in the samples were as follows:

|  | % Dimer and Higher Acids | |
| --- | --- | --- |
| Hours | Clarion 470 | Clarion 550 |
| 0 | 0 | 0 |
| 2 | 7 | 7 |
| 3 | 10 | 11 |
| 8 | 10 | 11 |
| 24 | 14 | 11 |

A trial was also run with Panther Creek clay. Formation of xylylstearic acid was significantly poorer than with the noted Clarion clays.

EXAMPLE 9

The procedure of Example 6, above, was carried out with various amounts of Clarion 470 as the clay. A 2:1 ratio of Clarion 470 clay to Pamolyn-100 never resulted in a dimer and higher acid concentration in the product of more than 5%. Reducing the ratio of Clarion 470 clay to Pamolyn-100 to 1:1 resulted in a doubling of the amount of dimer and higher acid concentration.

EXAMPLE 10

The procedure of Example 6, above, was carried out with various clays. At the end of the runs, product in solution and product on the clay were analyzed and compared. For Montmorillonite K10 clay, product in solution was about 95% xylylstearic acid and about 5% dimer and higher acids, while product on the clay was about 40% xylylstearic acid and 60% dimer and higher acids. For Clarion 470 clay, product in solution was about 85% xylylstearic acid and about 15% dimer and higher acids, while product on the clay was about 30% xylylstearic acid and 70% dimer and higher acids. For Clarion 550 clay, product in solution was about 87% xylylstearic acid and about 13% dimer and higher acids, while product on the clay was about 27% xylylstearic acid and 73% dimer and higher acids. The amount of product absorbed on the clay was found to be about 10% of the weight of the clay in each case.

EXAMPLE 11

Experiments were run to study the effect of varying the ratio of oleic acid to xylene and introducing the oleic acid slowly. Clarion 470 clay (58.1 gm) and xylene (250 gm) were placed in a three-necked flask equipped with a thermometer, a Dean-Stark tube and an inlet for the addition of fatty acid by means of a chemical pump. The clay and xylene mixture was refluxed under azeotropic conditions for a half hour until no more water appeared. Then, Pamolyn-100 (49.2 gm) was added at a constant rate over a 112 minute period by means of a chemical pump. Reflux then was continued for ten more hours. The solution next was allowed to cool to ambient temperature and stand for six hours. The xylene solution was decanted from the clay and filtered. Methanol (170 gm) was added to the remaining clay and the mixture was refluxed for five minutes to remove any material absorbed on the clay. The methanol solution was filtered and combined with the xylene solution. Evaporation of the methanol and xylene under a vacuum yielded 67.3 grams of an oily product. Analysis by IR and by HNMR showed complete reaction to xylylstearic acid. Analysis by GC showed less than 1% dimer acids.

Six further runs were carried out according to this procedure, except that the amount of Clarion 470 clay was varied (with the amount of xylene always at 250 grams) and in two of the runs, the oleic acid (Pamolyn-100) added all at once and in the other four runs, the rate of addition of the oleic acid was varied. The following results were obtained, wherein "addition time" identifies the number of hours over which the oleic acid was added (with 0 indicating that it was added all at once), "Clay/Oleic Ratio" identifies the weight ratio of Clarion 470 to Pamolyn-100, and "% Xylylstearic Acid" and "% Dimer" represents the percentage make-up of the product (including that on the clay as well as that in solution) that is attributable to xylylstearic acid and to dimer and higher acids, respectively.

|  | Addition Time | Clay/Oleic Ratio | % Xylylstearic Acid | % Dimer |
| --- | --- | --- | --- | --- |
| Run 1 | 0 | 2.0 | 82 | 18 |
| Run 2 | 0 | 1.0 | 75 | 25 |
| Run 3 | 2 | 1.2 | 99+ | * |
| Run 4 | 3 | 0.7 | 98 | 2 |
| Run 5 | 6 | 0.7 | 95 | 5 |
| Run 6 | 18 | 0.6 | 90 | 10 |

*less than 1%

In view of the above, it will be seen that the several advantages of the invention are achieved and other advantageous results attained.

As various changes could be made in the above methods and compositions without departing from the scope of the invention, it is intended that all matter contained in the above description shall be interpreted as illustrative and not in a limiting sense.

What is claimed is:

1. A method for preparing an aryl-substituted fatty acid or fatty ester, comprising introducing at a rate and over a period of time an olefinic composition selected from the group consisting of mono-unsaturated fatty acids, mono-unsaturated fatty esters and mixtures thereof to a reaction zone comprising a liquid aromatic hydrocarbon in contact with a catalytic amount of a zeolite or clay catalyst, thereby to cause a reaction, the reaction being allowed to proceed for a time and at a temperature, and the rate and the period of time of introduction of the olefinic compsition being sufficient, to produce a reaction product comprising at least a 70% yield of aryl-substituted fatty acid or fatty ester.

2. A method as set forth in claim 1 wherein the olefinic composition is introduced to the reaction zone over a period of at least an hour.

3. A method as set forth in claim 2 wherein the catalyst is a clay catalyst.

4. A method as set forth in claim 3 wherein the clay catalyst is selected from the group consisting of Montmorillonite K10, Clarion 470 and Clarion 550.

5. A method as set forth in claim 4 wherein the olefinic composition is selected from the group consisting of mono-unsaturated fatty acids of from about 14 to about 22 carbon atoms, mono-unsaturated fatty esters having an acid-derived moiety of from about 14 to about 22 carbon atoms, and mixtures thereof.

6. A method as set forth in claim 5 wherein the mono-unsaturated fatty esters are liquid glycerides or liquid alkyl esters of fatty acids of from about 14 to about 22 carbon atoms, the alkyl esters containing an alcohol-derived alkyl group of up to about ten carbon atoms.

7. A method as set forth in claim 6 wherein the mono-unsaturated fatty esters are alkyl esters that contain an alcohol-derived alkyl group of up to about eight carbon atoms.

8. A method as set forth in claim 5 wherein the olefinic composition comprises a mono-unsaturated fatty acid.

9. A method as set forth in claim 8 wherein the olefinic composition is oleic acid and the reaction product comprises a desired yield of aryl-substituted stearic acid.

10. A method as set forth in claim 4 wherein the liquid aromatic hydrocarbon is selected from the group consisting of benzene compounds and naphthalene compounds.

11. A method as set forth in claim 10 wherein the liquid aromatic hydrocarbon is a benzene compound.

12. A method as set forth in claim 11 wherein the liquid aromatic hydrocarbon is selected from the group consisting of benzene, toluene, xylene and cumene.

13. A method as set forth in claim 6 wherein the liquid aromatic hydrocarbon is selected from the group consisting of benzene compounds and naphthalene compounds.

14. A method as set forth in claim 4 wherein the olefinic composition is added to the liquid aromatic hydrocarbon containing clay over a period of at least two hours.

15. A method as set forth in claim 14 wherein the temperature is about 130° C. to about 250° C. and the reaction is carried out at an pressure of from about 50 to about 200 psig.

16. A method as set forth in claim 5 wherein at most about one mole of fatty acid per mole aromatic hydrocarbon in the reaction zone is introduced into the reaction zone.

17. A method as set forth in claim 5 wherein the clay catalyst is present in a concentration of from about 1% to about 8% by weight based on the total weight of the olefinic composition, the liquid aromatic hydrocarbon and the clay.

18. A method as set forth in claim 15, further comprising the step of separating the clay from the aryl-substituted fatty acid or fatty ester in the reaction product to produce a clay-free filtrate.

19. A method as set forth in claim 18, further comprising the step of distilling off excess liquid aromatic hydrocarbon from the filtrate.

20. A method as set forth in claim 3 wherein the reaction is allowed to proceed for a time and at a temperature, and the period of time of introduction of the olefinic composition is sufficient, to produce a reaction product comprising at least a 80% yield of aryl-substituted fatty acid or fatty ester.

21. A method for preparing an aryl-substituted fatty acid or fatty ester, comprising introducing at a rate or period of time an olefinic composition selected from the group consisting of mono-unsaturated fatty acids, mono-unsaturated fatty esters and mixtures thereof to a reaction zone free of phosphorus oxyacids and comprising a liquid aromatic hydrocarbon and a catalytic amount of a zeolite or clay catalyst, thereby to cause a reaction, the reaction being allowed to proceed for a time and at a temperature, and the rate and the period of time of introduction of the olefinic composition being sufficient, to produce a reaction product comprising at least a 50% yield of aryl-substituted fatty acid or fatty ester.

22. A method as set forth in claim 21 wherein the olefinic composition is introduced to the reaction zone over a period of at least an hour.

23. A method as set forth in claim 22 wherein the catalyst is a clay catalyst.

24. A method as set forth in claim 23 wherein the clay catalyst is selected from the group consisting of Montmorillonite K10, Clarion 470 and Clarion 550.

25. A method for preparing an aryl-substituted fatty acid or fatty ester, comprising introducing over a period of time an olefinic composition selected from the group consisting of mono-unsaturated fatty acids, mono-unsaturated fatty esters and mixtures thereof to a reaction zone free of phosphorus oxyacids and comprising a liquid aromatic hydrocarbon and a reaction catalyst consisting essentially of a catalytic amount of a zeolite or clay catalyst, thereby to cause a reaction, the reaction being allowed to proceed for a time and at a temperature, and the period of time of introduction of the olefinic composition being sufficient, to produce a reaction product comprising at least a 50% yield of aryl-substituted fatty acid or fatty ester.

26. A method as set forth in claim 25 wherein the olefinic composition is introduced to the reaction zone over a period of at least an hour.

27. A method as set forth in claim 26 wherein the reaction catalyst consists essentially of a catalytic amount of a clay catalyst.

28. A method as set forth in claim 27 wherein the clay catalyst is selected from the group consisting of Montmorillonite K10, Clarion 470 and Clarion 550.

29. A method for prepareing an aryl-substituted fatty acid or fatty ester, comprising the steps of:
   (a) bringing a liquid aromatic hydrocarbon into contact with a catalytic amount of a catalyst which is a zeolite or clay catalyst to form a catalyzed aromatic composition comprising the catalyst and the liquid aromatic hydrocarbon, and
   (b) adding, over a period of at least about an hour, an olefinic composition selected from the group consisting of mono-unsaturated fatty acids, mono-unsaturated fatty esters and mixtures thereof to the catalyzed aromatic composition is maintained at a temperature sufficient to produce a reaction product comprising at least a 70% yield of aryl-substituted fatty acid or fatty ester.

30. A method as set forth in claim 29 wherein the catalyst is a clay catalyst and the process produces more than an 80% yield of aryl-substituted fatty acid or fatty ester.

31. A method as set forth in claim 30 wherein the olefinic composition is introduced to the reaction zone over a period of at least two hours.

32. A method as set forth in claim 31 wherein the clay catalyst is selected from the group consisting of Montmorillonite K10, Clarion 470 and Clarion 550.

33. A method as set forth in claim 29 wherein the catalyzed aromatic composition consists essentially of the catalyst and the liquid aromatic hydrocarbon.

* * * * *

UNITED STATES PATENT AND TRADEMARK OFFICE
CERTIFICATE OF CORRECTION

PATENT NO. : 5,840,942
DATED : November 24, 1998
INVENTOR(S) : Bernardus Oude Alink It is certified that error appears in the above-identified patent and that said Letters Patent is hereby corrected as shown below:

In claim 1, line 10; replace "compsition" with ---composition---;

In claim 15, line 3; replace "an" with ---a---; and

In claim 29, line 11 between the words "to" and "the", insert the phrase --- the catalyzed aromatic compositions, while---.

Signed and Sealed this

Fourth Day of May, 1999

Q. TODD DICKINSON

*Attest:*

*Attesting Officer*  Acting Commissioner of Patents and Trademarks